US009939398B2

(12) United States Patent
Dempster et al.

(10) Patent No.: US 9,939,398 B2
(45) Date of Patent: Apr. 10, 2018

(54) DETECTING MOISTURE WITH AN ANTENNA

(71) Applicant: HzO, Inc., Draper, UT (US)

(72) Inventors: James Douglas Dempster, Reno, NV (US); Jason Maynard, Salt Lake City, UT (US)

(73) Assignee: HZO, INC., Draper, UT (US)

( * ) Notice: Subject to any disclaimer, the term of this patent is extended or adjusted under 35 U.S.C. 154(b) by 0 days.

(21) Appl. No.: 14/626,520

(22) Filed: Feb. 19, 2015

(65) Prior Publication Data

US 2016/0077029 A1 Mar. 17, 2016

Related U.S. Application Data (60) Provisional application No. 62/049,811, filed on Sep. 12, 2014.

(51) Int. Cl.
G01N 27/04 (2006.01)
G01N 22/04 (2006.01)

(52) U.S. Cl.
CPC ........... G01N 27/048 (2013.01); G01N 22/04 (2013.01)

(58) Field of Classification Search
None
See application file for complete search history.

(56) References Cited

U.S. PATENT DOCUMENTS

| 4,297,686 A | 10/1981 | Tom |
| 4,466,285 A | 8/1984 | Allemano |
| 4,835,716 A | 5/1989 | Tamaki et al. |
| 4,918,433 A | 4/1990 | Moore |
| 5,097,254 A | 3/1992 | Merrithew |
| 5,847,473 A | 12/1998 | Anfosso et al. |
| 6,526,807 B1 | 3/2003 | Doumit et al. |
| 6,603,319 B1 | 8/2003 | Kasahara et al. |
| 6,614,722 B2 | 9/2003 | Polany et al. |
| 6,683,535 B1 | 1/2004 | Utke |
| 6,843,694 B2 | 1/2005 | Simmons |
| 7,142,123 B1 | 11/2006 | Kates |
| 7,554,453 B2 | 6/2009 | Snyder et al. |
| 7,642,921 B2 | 1/2010 | Cutler et al. |
| 7,671,754 B2 | 3/2010 | Heilmann et al. |
| 7,889,087 B2 | 2/2011 | Boss et al. |

(Continued)

FOREIGN PATENT DOCUMENTS

| CN | 2702453 Y | 5/2005 |
| CN | 201657083 U | 11/2010 |

(Continued)

OTHER PUBLICATIONS

Jinlan, Gau et al., "Printed Humidity Sensor with Memory Functionality for Passive RFID Tags", dated May 1, 2015, pp. 1824-1834, vol. 13, No. 5, IEEE Sensors Journal, IEEE Service Center, New York, NY.

(Continued)

*Primary Examiner* — Jermele M Hollington
*Assistant Examiner* — Douglas X Rodriguez
(74) *Attorney, Agent, or Firm* — Kunzler, PC (57) ABSTRACT

Methods and systems may be provided that detect moisture with an antenna. Electrical impedance at the antenna may be detected by an impedance sensor. Moisture may be detected based on the impedance at the antenna.

16 Claims, 7 Drawing Sheets

(56) References Cited

U.S. PATENT DOCUMENTS

| | | | |
|---|---|---|---|
| 8,063,765 B2 | 11/2011 | Johnson et al. | |
| 8,118,681 B2 | 2/2012 | Mattice et al. | |
| 8,255,006 B1 | 8/2012 | Chavez et al. | |
| 8,330,475 B2 | 12/2012 | Van Bezooijen et al. | |
| 8,359,172 B2 | 1/2013 | Fattah | |
| 8,374,553 B1 | 2/2013 | Campbell et al. | |
| 8,440,274 B2 | 5/2013 | Wang | |
| 8,482,305 B2 | 7/2013 | Johnson | |
| 8,625,393 B2 | 1/2014 | Sonnenschein et al. | |
| 8,643,712 B2 | 2/2014 | Tsai | |
| 8,731,342 B2 | 5/2014 | Yang et al. | |
| 8,773,271 B1 | 7/2014 | Stevens et al. | |
| 8,781,420 B2 | 7/2014 | Schlub et al. | |
| 8,958,854 B1 | 2/2015 | Morley et al. | |
| 2003/0024315 A1 | 2/2003 | Merkel et al. | |
| 2003/0117321 A1* | 6/2003 | Furse | H01Q 1/36 343/700 MS |
| 2003/0222662 A1* | 12/2003 | Geisel | G01N 27/048 324/664 |
| 2005/0079888 A1 | 4/2005 | Menz et al. | |
| 2006/0079888 A1 | 4/2006 | Mulier et al. | |
| 2008/0088462 A1 | 4/2008 | Breed | |
| 2009/0207031 A1 | 8/2009 | Barth et al. | |
| 2010/0176956 A1 | 7/2010 | Moerschell | |
| 2010/0225335 A1* | 9/2010 | Boschetti | G01N 33/46 324/664 |
| 2010/0248792 A1 | 9/2010 | Yamashita | |
| 2011/0067576 A1 | 3/2011 | White et al. | |
| 2011/0105100 A1 | 5/2011 | Tanaka et al. | |
| 2011/0109333 A1 | 5/2011 | Porjo et al. | |
| 2011/0137472 A1 | 6/2011 | Hitt et al. | |
| 2011/0268292 A1 | 11/2011 | Suvanto et al. | |
| 2012/0178367 A1 | 7/2012 | Matsumoto et al. | |
| 2012/0218673 A1 | 8/2012 | Oguri | |
| 2012/0231841 A1 | 9/2012 | Neiderberger et al. | |
| 2012/0286949 A1 | 11/2012 | Worthington et al. | |
| 2012/0324384 A1 | 12/2012 | Cohen et al. | |
| 2013/0151870 A1 | 6/2013 | Chuang | |
| 2013/0182360 A1* | 7/2013 | Stevens | H02H 5/00 361/71 |
| 2013/0210297 A1 | 8/2013 | Maas et al. | |
| 2013/0225237 A1 | 8/2013 | Minami | |
| 2013/0286576 A1 | 10/2013 | Toya | |
| 2013/0325265 A1 | 12/2013 | Percher | |
| 2014/0057688 A1 | 2/2014 | Shinoda et al. | |
| 2014/0120866 A1 | 5/2014 | Furtney | |
| 2014/0185177 A1 | 7/2014 | Li | |
| 2014/0186177 A1 | 7/2014 | Bohme et al. | |
| 2014/0191873 A1 | 7/2014 | Kreiner et al. | |
| 2014/0237304 A1 | 8/2014 | Lai et al. | |
| 2014/0307356 A1 | 10/2014 | Hong et al. | |
| 2014/0327991 A1 | 11/2014 | Chung | |
| 2015/0016000 A1 | 1/2015 | Quirk et al. | |

FOREIGN PATENT DOCUMENTS

| | | |
|---|---|---|
| DE | 3605633 A1 | 9/1987 |
| EP | 0 316 551 | 5/1989 |
| EP | 1158511 A2 | 11/2001 |
| JP | H05 281172 A | 10/1993 |
| WO | WO 2011/064737 A2 | 6/2011 |

OTHER PUBLICATIONS

Pandey, Gunjan et al., "A low profile, low RF band, small antenna for underground, in-situ sensing and wireless energy-efficient transmission", dated Apr. 7, 2014, pp. 179-184, Proceedings of the 11$^{th}$ IEEE International Conference on Networking, Sensing and control, IEEE, New York, NY.

International Search Report, dated Jun. 1, 2015, pp. 1-12, International Patent Application No. PCT/US2015/016874, European Patent Office, Rijswijk, Netherlands.

Neil Hughes, "Apple looking to improve water sensors for detecting iPhone damage," dated Feb. 17, 2012, pp. 1-10, Apple Insider, http://appleinsider.com.

Kevin Purcell, "How to Find Your Mobile Phone's Water Sensor," dated Aug. 16, 2010, pp. 1-3, www.Notebooks.com.

Matthew Braga, "Stay Dry: Where to Find Your Phone's Water Sensors," dated Aug. 16, 2010, pp. 1-8, www.Tested.com.

"Depth/Level Druck Submersible Pressure Sensors Product Guide," dated 2005, pp. 1-6, GE Sensing.

* cited by examiner

DETECTING MOISTURE WITH AN ANTENNA

This application claims priority to U.S. Provisional Application 62/049,811, entitled "Water Sensing and Notification," filed Sep. 12, 2014, and which is incorporated herein by reference in its entirety.

BACKGROUND

1. Technical Field

This application relates to sensors and, in particular, to moisture sensors.

2. Related Art

A communication apparatus may be damaged due to moisture, heat, or any other adverse physical conditions. For example, when the communication apparatus is immersed in liquid or is exposed to excessive moisture, then the communication apparatus may be irreparably damaged. Corrosion and/or a short circuit may physically damage a component of the communication apparatus. In some designs, the communication apparatus may be disabled proactively when exposed to moisture even though the moisture would not have actually damaged the communication apparatus.

SUMMARY

A system for moisture detection may be provided that includes an antenna, an impedance sensor, and a control circuit. The impedance sensor may detect an electrical impedance at the antenna. The control circuit may detect moisture based on the impedance at the antenna.

A computer readable storage medium may be provided that includes instructions executable by a processor to receive an impedance from an impedance sensor, where the impedance is electrical impedance at an antenna detected by the impedance sensor. The computer readable storage medium may include instructions executable to detect moisture based on the impedance at the antenna.

A method to detect moisture with an antenna may be provided. Electrical impedance at the antenna may be detected by an impedance sensor. Moisture may be detected by a processor based on the impedance at the antenna.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

DETAILED DESCRIPTION

Methods and/or systems are provided to detect moisture with an antenna. Electrical impedance at the antenna may be detected by an impedance sensor. For example, a signal may be transmitted by the antenna that has voltage and current. The impedance sensor may measure the voltage and current and derive the impedance by dividing voltage by current. Moisture may be detected by a processor based on the impedance at the antenna. For example, if the impedance drops below a threshold value, then the processor may detect moisture. Alternatively, if the impedance remains above the threshold value, then the processor may not detect moisture.

One technical advantage of the systems and methods described herein may be that moisture may be quickly detected. The impedance at the antenna(s) changes at substantially the same time as the moisture changes. Quickly detecting moisture may be helpful to avoid short circuits or other types of damage resulting from moisture. Another technical advantage of the systems and methods described herein may be that the antenna(s) is/are already present in a communication device and can used for both moisture detection and for transmitting and/or receiving data.

Figure 1:
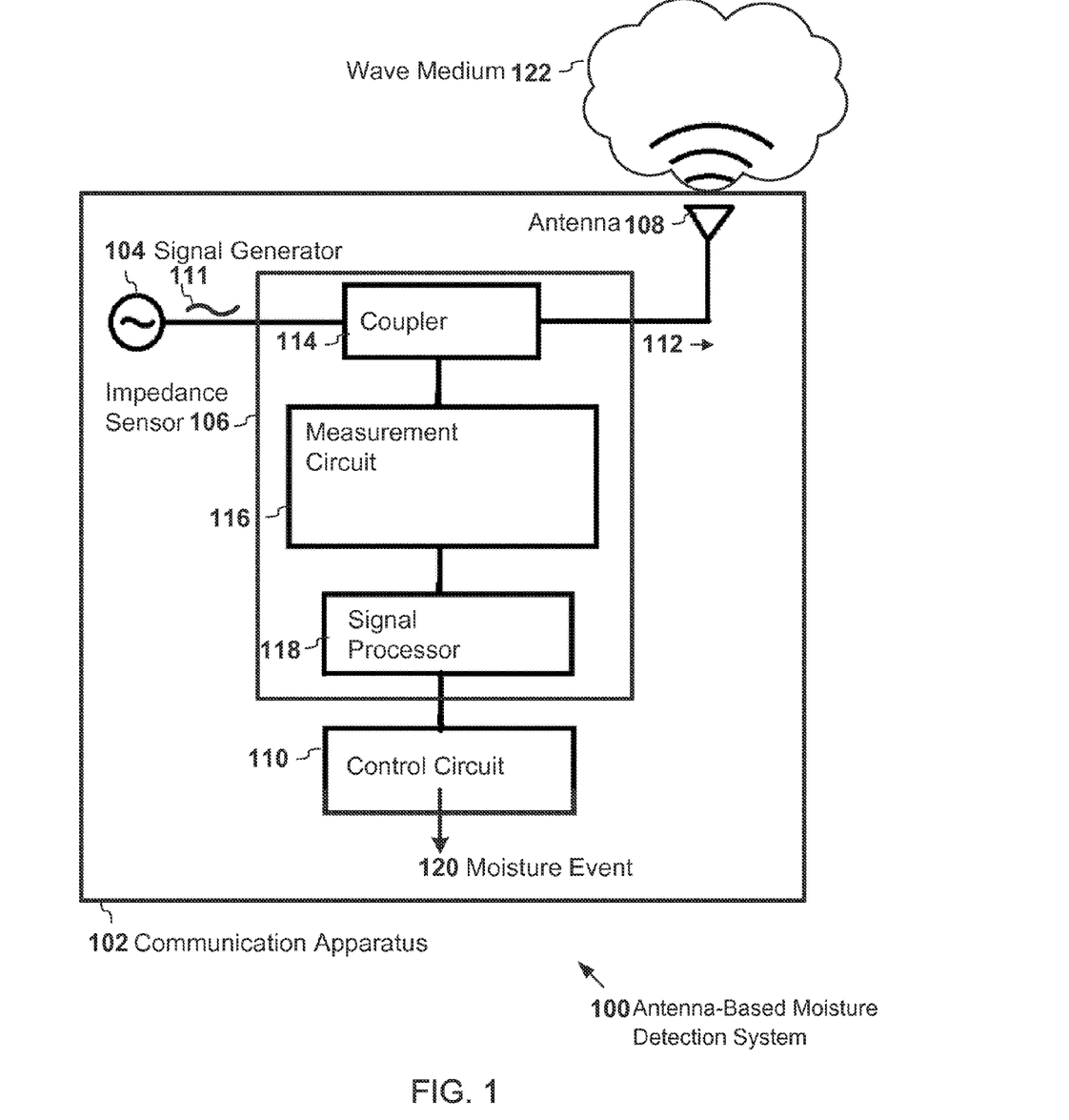
FIG. 1 illustrates an antenna-based moisture detection system.

FIG. 1 illustrates an antenna-based moisture detection system 100. The system 100 may include a communication apparatus 102. The communication apparatus 102 may include a signal generator 104, an impedance sensor 106, an antenna 108, and a control circuit 110. The control circuit 110 may be electrically coupled to the impedance sensor 106. The impedance sensor 106 may be electrically coupled to the signal generator 104 and the antenna 108.

The communication apparatus 102 may be one or more devices that communicate with other devices via the antenna 108. The communication apparatus 102 may be in the form of a mobile device, a mobile phone, a cell phone, a smart phone, a personal digital assistant, a camera, a marine radio, a navigation system (such as a global positioning system), a media player, a tablet computer, a laptop, a desktop computer, or any other device or combination of devices that includes or is coupled to the antenna 108.

The signal generator 104 may be any device that generates a signal that may be transmitted by the antenna 108. The signal generator 104 may be, for example, a transmitter circuit, a transceiver circuit, or a RF (radio frequency) signal generator circuit. The signal generated by the signal generator 104 may be an antenna signal 111 conveyed to the antenna 108 via one or more conductive elements where the antenna signal 111 is then broadcast or transmitted. In some examples, the signal generator 104 may be any typical radio frequency (RF) signal generator circuitry. In some examples, the signal generator 104 may be specifically tuned to a frequency band suitable to the type of antenna with which the signal generator 104 is electrically coupled.

The antenna 108 may be any type of antenna, such as an antenna commonly found in a portable electronic device. Examples of the antenna 108 may include a cellular network antenna, a wireless network antenna such as a WI-FI® antenna, a Bluetooth® antenna, a GPS (Global Positioning System) antenna, and/or any other type of antenna over which data and/or packets of data are communicated. WI-FI is a registered trademark of Wireless Ethernet Compatibility Alliance, Inc. of Austin, Tex. BLUETOOTH is a registered trademark of Bluetooth Sig, Inc. of Kirkland, Wash.

The impedance sensor 106 may be any component that detects electrical impedance 112 at the antenna 108. For example, the impedance sensor 106 may be any component that detects the magnitude of the antenna signal 111 at the antenna 108 and/or the phase of the antenna signal 111 at the antenna 108. The detection of the impedance 112 by the impedance sensor 106 may include detection of one or more patterns in the impedance 112 across frequencies and/or over time. The impedance sensor 106 may include a coupler 114, a measurement circuit 116, and a signal processor 118.

The coupler 114 may be a component that detects the antenna signal 111 or a property thereof. An example of the coupler 114 may be a resistor coupled between two inputs of an operational amplifier. The coupler 114 may serve as a tap that routes, for example, a fraction of the antenna signal 111 generated by the signal generator 104 to the measurement circuit 116.

The measurement circuit 116 may be any component that measures one or more properties of the antenna signal 111. For example, the measurement circuit 116 may include phase and magnitude detector circuitry. The measurement circuit 116 may be any circuitry designed to take phase and/or magnitude measurements of the antenna signal 111.

The signal processor 118 may be any processor that operates on the one or more properties of the antenna signal 111 measured by the measurement circuit 116. Examples of the signal processor 118 may include an analog-to-digital converter, a digital signal processor, and/or any other processor. The analog-to-digital converter, for example, may convert the impedance 112 to one or more digital values that the control circuit 110 may receive. In another example, the signal processor 118 may detect whether a pattern occurs in the impedance 112 over time and/or across frequencies.

Figure 6:
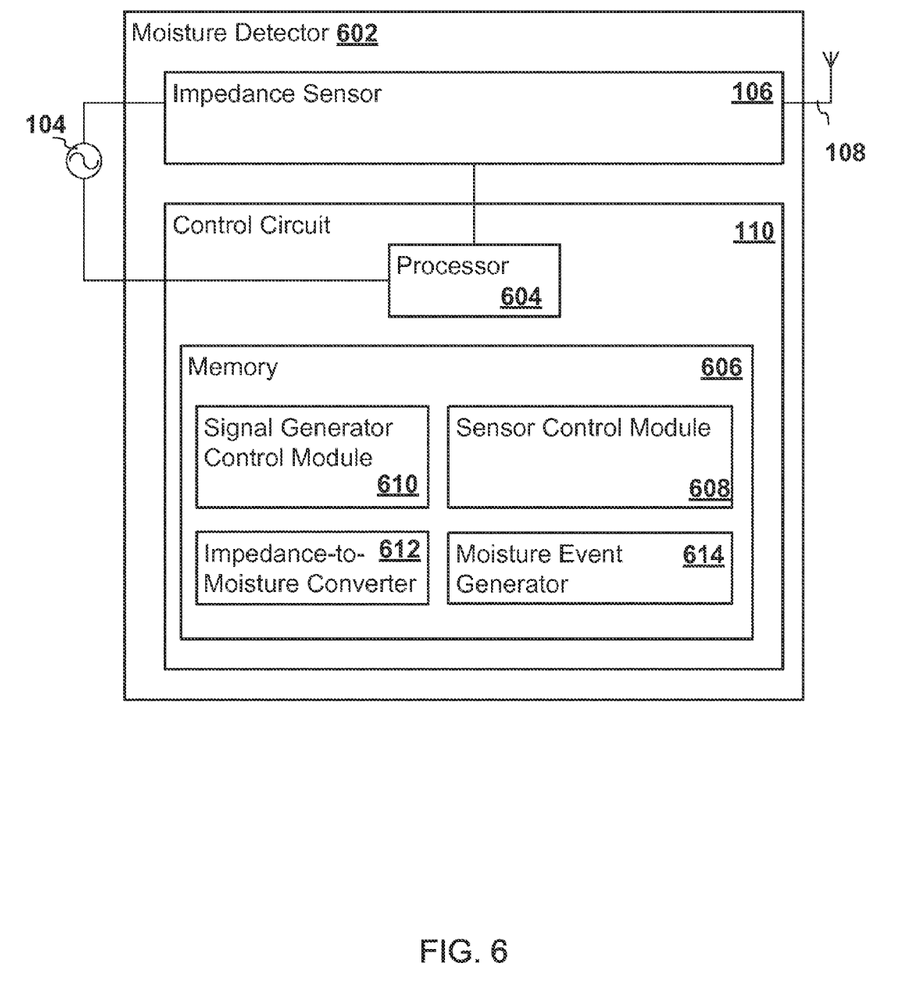
FIG. 6 illustrates an example of a control circuit of an antenna-based moisture detection system.

The control circuit 110 may be a component that determines whether to generate a moisture event 120 based on the impedance 112 at the antenna 108. An example of the control circuit 110 is illustrated in FIG. 6.

The moisture event 120 may be a signal or any other indication of moisture level and/or of a change in the moisture level in and/or around the communication apparatus 102. In some examples, the moisture event 120 may indicate an immersion event was detected, which may occur if the communication apparatus 102 is at least partially immersed in a liquid. Alternatively or in addition, the moisture event 120 may indicate the moisture level in and/or around the communication apparatus 102 exceeds a threshold amount. Alternatively or in addition, the moisture event 120 may indicate that a change in the moisture level was detected.

During operation of the moisture detection system 100, an environment in which the communication apparatus 102 operates may change. The environment may change when the communication apparatus 102 is completely or partially immersed in a liquid. For example, the communication apparatus 102 may move from air to liquid, such as when the communication apparatus 102 is dropped from the air into liquid or if liquid splashes onto the communication apparatus 102. In another example, the environment may change when the humidity of the air in and/or around the communication apparatus 102 changes. The humidity may change, for example, when the communication apparatus 102 moves from a dry area to a humid area, such as when flying from a desert to the tropics or when moving from a relatively cold outdoor environment to a relatively warm, humid interior of a building.

The environment in and/or around the communication apparatus 102 includes a wave medium 122. The wave medium 122 transports electromagnetic waves transmitted and/or received by the antenna 108. The wave medium may be air, water, a combination of air and water, a vacuum, and/or any other type of medium through which electromagnetic waves may propagate. As the environment in and/or around the communication apparatus 102 changes, one or more properties of the wave medium 122 may change. Corresponding to the change(s) in the wave medium 122, the electrical impedance 112 at the antenna 108 may correspondingly change. The impedance 112 at the antenna 108 may be a complex quantity, Z, where $Z=V/I$ at a particular frequency $\omega$, where V is voltage and I is current. The impedance 112, Z, may include a magnitude and/or a phase. Alternatively or in addition, the impedance 112 may be a real or integer value. The impedance 112 at the antenna 108 may be the impedance of the antenna 108. Alternatively, the impedance 112 at the antenna 108 may be the impedance of the wave medium 122 as seen by the antenna 108.

The impedance 112 may vary by the frequency of the antenna signal 111. Alternatively or in addition the impedance 112 may be substantially constant over one or more frequency ranges. In some examples, signal phase shifts and/or magnitude shifts of the antenna signal 111 may be measured and/or detected by the impedance sensor 106.

If humidity in the environment around the communication apparatus 102 increases, then the magnitude of the impedance 112 at the antenna 108 may decrease. Similarly, if the environment changes from air to a liquid, then the magnitude of the impedance 112 at the antenna 108 may decrease.

The impedance sensor 106 may detect the impedance 112 before and after the environment change and/or detect the change in impedance 112 due to the environment change. The impedance sensor 106 may transmit the impedance 112 to the control circuit 110. The impedance 112 may be actual measured impedance, an indication of the impedance 112, and/or an indication of a change in the impedance 112. For example, the impedance 112 may be a relative indication of actual impedance, such as high, medium, and low. The impedance sensor 106 may be designed and coupled to the antenna 108 with the coupler 114 in such a way that the impedance sensor 106 does not interfere with the normal operation of the antenna 108. In other words, the impedance sensor 106 may not substantially interfere with transmission and/or receipt of data at the antenna 108.

The impedance sensor 106 may detect the impedance 112 based on the antenna signal 111 generated by the signal generator 104 or any other signal derived therefrom. For example, the impedance sensor 106 may measure voltage, V, and current, I, of the antenna signal 111, and derive the impedance 112 from the voltage V and current I.

Alternatively or in addition, the impedance sensor 106 may detect the impedance 112 based on one or more signals received from the antenna 108 by the coupler 114. The signals received from the antenna 108 may include, for example, antenna signals reflected from the antenna 108 that are generated by the signal generator 104 and/or signals that are received by the antenna 108 from another signal source. The signals received from the antenna 108 may be routed to the measurement circuit 116. The measurement circuit 116 may monitor the values of the reflected signals and/or the received signals. The measurement circuit 116 may generate corresponding measured phase and/or magnitude information, which may be passed to the signal processor 118 and/or to the control circuit 110.

The existence of the reflected signals having a magnitude that exceeds a threshold value may indicate an impedance mismatch between the antenna 108 and signal generator 104. A design goal of the communication apparatus 102 may be to match an impedance of the signal generator 104 with the impedance 112 of the antenna 108. The impedance matching design goal may result in limiting the magnitude and/or the existence of the reflected signals, which may result in efficient transfer of power from the antenna signal 111 to electromagnetic waves that propagate in the wave medium 122. Because the impedance 112 of the antenna 108 depends at least in part on one or more properties of the wave medium 122, the impedance matching design may be performed based on one or more assumptions about the wave medium 122 under normal operating conditions. If the moisture level in the wave medium 122 deviates from normal operating conditions, then an impedance mismatch and the reflected signals may result. Therefore, if the impedance sensor 106 detects the existence of the reflected signals and/or the magnitude of one or more of the reflected signals exceed the threshold value, then the impedance sensor 106 may detect the impedance 112 and/or a change in the impedance 112. Alternatively or in addition, the impedance sensor 106 may detect the impedance 112 by measuring the voltage and current of the reflected signal(s) and determine the impedance 112 therefrom.

The control circuit 110 may detect moisture based on the impendence 112 detected at the antenna 108. For example, in response to a decrease in the impedance 112 detected by the impedance sensor 106 over time, the control circuit 110 may determine that moisture is detected. A decrease in the impedance 112 over time may indicate a relative increase in moisture level of the wave medium 122. In some examples, the control circuit 110 may map the impedance 112 to a moisture level. The mapping may be via a table comprising impedance values or value ranges and corresponding moisture levels. Alternatively or in addition, the mapping may be a mathematical equation expressing the moisture level as a function of the impedance 112. In another example, in response to the magnitude of the impedance 112 falling below a threshold magnitude, the control circuit 110 may determine that moisture is detected and/or that the communication apparatus 102 is at least partially immersed in liquid. The threshold magnitude may vary by implementation. A suitable threshold magnitude may be determined by, for example, measuring the impedance 112 when the antenna 108 is in air and again when the antenna 108 is immersed and/or when the moisture level in the wave medium 122 otherwise exceeds a target moisture level. The threshold magnitude may be set to the measured impedance when the moisture level exceeds the target moisture level.

In yet other examples, the control circuit 110 may determine that moisture is detected in response to detecting a pattern of impedance 112 changes across multiple frequencies. In one such example, if the magnitude of the impedance 112 drops substantially uniformly across a predetermined frequency range, then the control circuit 110 may determine that moisture is detected. Whereas in contrast, if the magnitude of the impedance 112 drops at differing amounts across the predetermined frequency range, then the control circuit 110 may determine that moisture is not detected. If the antenna 108 is placed next to a human head, for example, then the magnitude of the impedance 112 may drop at differing amounts across the predetermined frequency range. On the other, if the antenna 108 is splashed with water, then the magnitude of the impedance 112 may drop substantially the same amount across the predetermined frequency range.

In other words, a type of wave medium, such as a human head, a shirt pocket, or a metal cabinet, may have a corresponding characteristic impedance attenuation pattern in the frequency spectrum. The control circuit 110 may distinguish between moisture events or between moisture events and non-moisture events based on the characteristic impedance attenuation pattern in the frequency spectrum.

If the control circuit 110 determines that moisture is present, then in response, then the control circuit may transmit the moisture event 120 to another component of the communication apparatus 102. For example, the control circuit 110 may transmit the moisture event 120 to a central processing unit (not shown) of the communication apparatus 102. In another example, the control circuit 110 may transmit the moisture event 120 to a switch that disconnects power from one or more components of the communication apparatus 102 in response to the moisture event 120. In still another example, the control circuit 110 may transmit the moisture event 120 to a software application executed on the communication apparatus 102. For example, the control circuit 110 may invoke a programmatic procedure passing the moisture event 120 as an argument of the programmatic procedure.

In some examples, an alert may be generated in response to the moisture event 120. The alert may inform an operating system of the communication apparatus 102 and/or a user of the communication apparatus 102. In response to the alert, the user and/or the operating system may take appropriate action, such as shutting down power to the communication apparatus 102 or to one or more components of the communication apparatus 102.

The example of the communication apparatus 102 illustrated in FIG. 1 includes a single antenna. The single antenna is the antenna 108 at which the impedance sensor 106 detects the impedance 112. The single antenna is also the antenna 108 that transmits the antenna signal 111 generated by the signal generator 104. In different examples, the impedance sensor 106 may detect the impedance 112 at an antenna other than the antenna 108 that transmits the antenna signal 111 generated by the signal generator 104.

Figure 2:
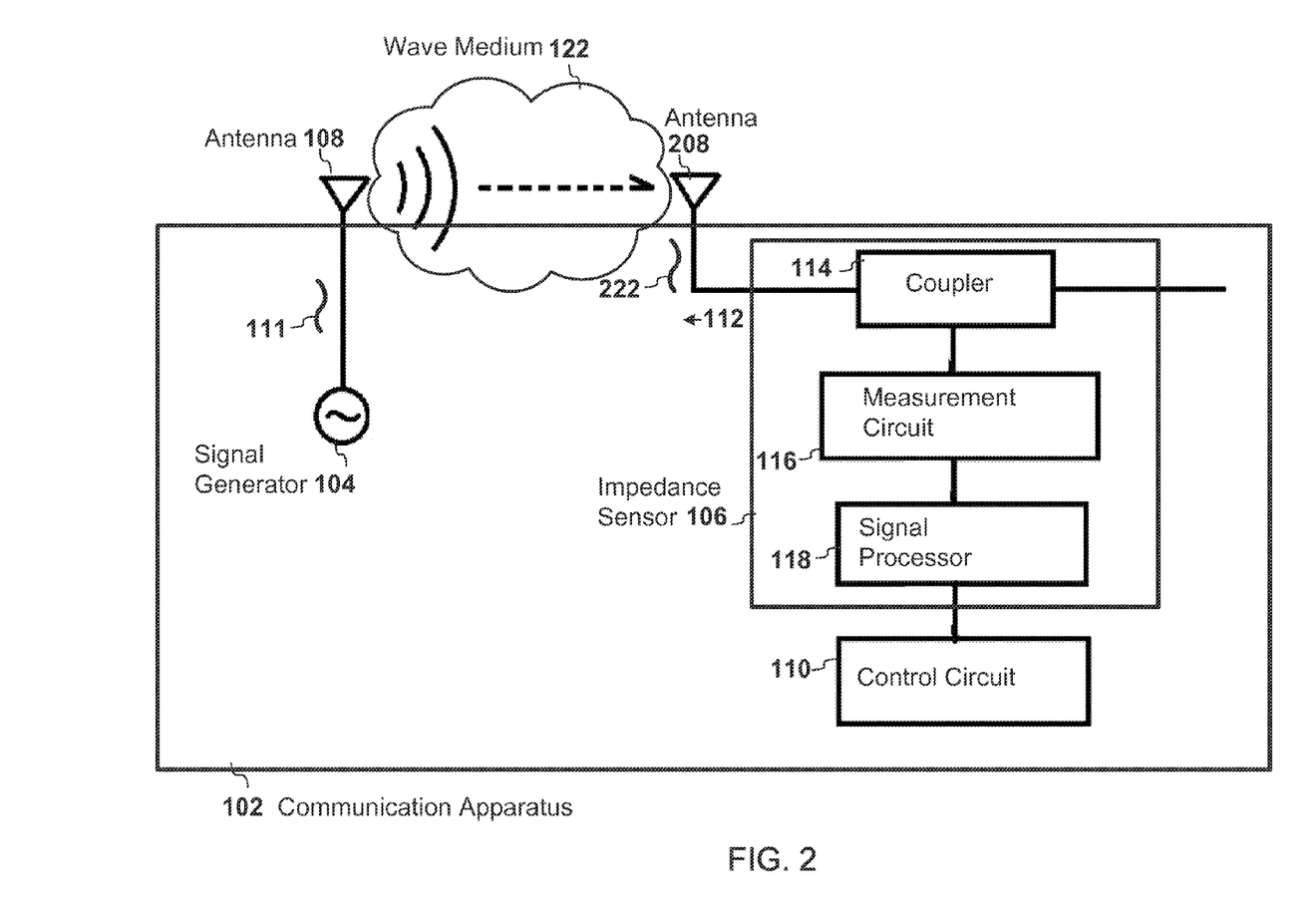
FIG. 2 illustrates a communication apparatus in an antenna-based moisture detection system that includes multiple antennas.

FIG. 2 illustrates an example of the communication apparatus 102 that includes multiple antennas 108 and 208. The antenna 208 at which the impedance sensor 106 detects the impedance 112 is different than the antenna 108 that transmits or broadcasts the antenna signal 111 generated by the signal generator 104. Accordingly, the impedance sensor 106 detects the impedance 112 at the antenna 208 that receives a signal 222 from the antenna 108, not the antenna 108 that transmits the antenna signal 111 generated by the signal generator 104.

The measurement circuit 116 of the impedance sensor 106 may measure the signal strength and/or the phase of the signal 222. The impedance sensor 106 may determine the impedance 112 by, for example, dividing the voltage of the signal 222 by the current of the signal 222. When the moisture content in the wave medium 122 between the antennas 108 and 208 changes, such as in response to immersion in a liquid or a change in ambient humidity, a corresponding change in the magnitude and/or the phase of the signal 222 received by the antenna 208 may result.

In some examples, the corresponding change in the magnitude and/or the phase of the signal 222 received by the antenna 208 may be identified by the impedance sensor 106 and/or the control circuit 110. In order to determine if the change in the magnitude and/or phase of the signal 222 is due to a change in the impedance 112 at the antenna 208 instead of a change in the antenna signal 111, the impedance sensor 106 may monitor the antenna signal 111 generated by the signal generator 104. For example, the impedance sensor 106 may determine the impedance 112 by comparing the voltage of the antenna signal 111 with the voltage of the signal 222 received by the antenna 208. Based on the comparison, the higher the attenuation of the signal 222 received by the antenna 208 relative to the voltage of the antenna signal 111, the higher the impedance 112.

In some examples, the impedance sensor 106 may isolate the signal 222 received by the antenna 208 from other signals received by the antenna 208 based on the antenna signal 111. For example, the impedance sensor 106 may block signals other than the signal 222 received from the antenna 108 that transmits the antenna signal 111 using signal processing techniques that rely on the antenna signal 111 and the received signal 222.

In some examples, the communication apparatus 102 may include multiple antennas like the antenna 208 in FIG. 2 that receives the signal 222. One antenna may be broadcasting while multiple antennas receive signals simultaneously, or substantially simultaneously, from the antenna 108 that broadcasts the antenna signal 111. The impedance sensor may determine the impedance of each of the receiving antennas separately and/or determine an overall impedance of the antennas.

Figure 3:
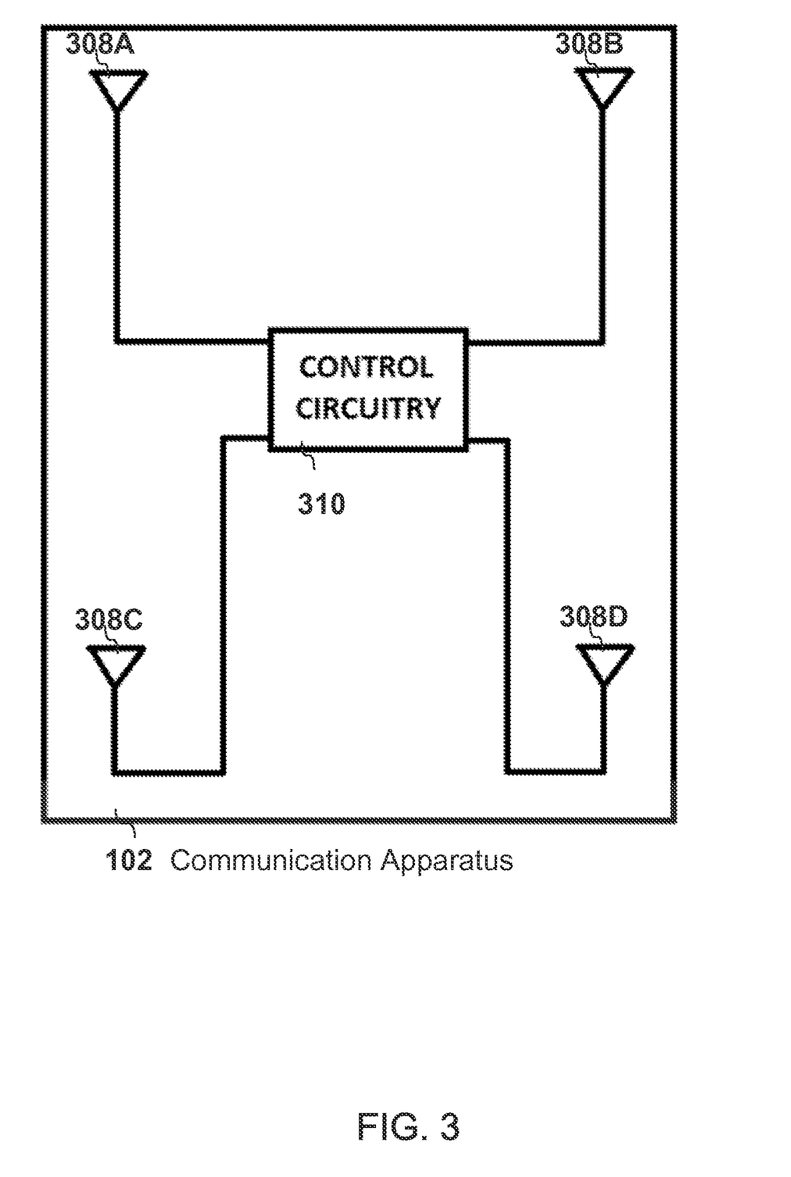
FIG. 3 illustrates an example placement of four antennas in and/or on a communication apparatus.

FIG. 3 illustrates an example placement of four antennas 308A, 308B, 308C, and 308D in and/or on the communication apparatus 102. Multiple antennas 308A, 308B, 308C, and 308D are typically present in a cellular device. Having two cellular antennas in the communication apparatus 102 is common, where one is a transmitter/receiver and another is a dedicated receiver. The communication apparatus 102 may include control circuitry 310 coupled to the antennas 308A, 308B, 308C, and 308D. The control circuitry 310 may include, for example, the control circuit 110 and an impedance sensor for one or more of the antennas 308A, 308B, 308C, and 308D. The control circuit 110 may detect moisture based on the impedance 112 measured by the one or more impedance sensors.

Figure 4:
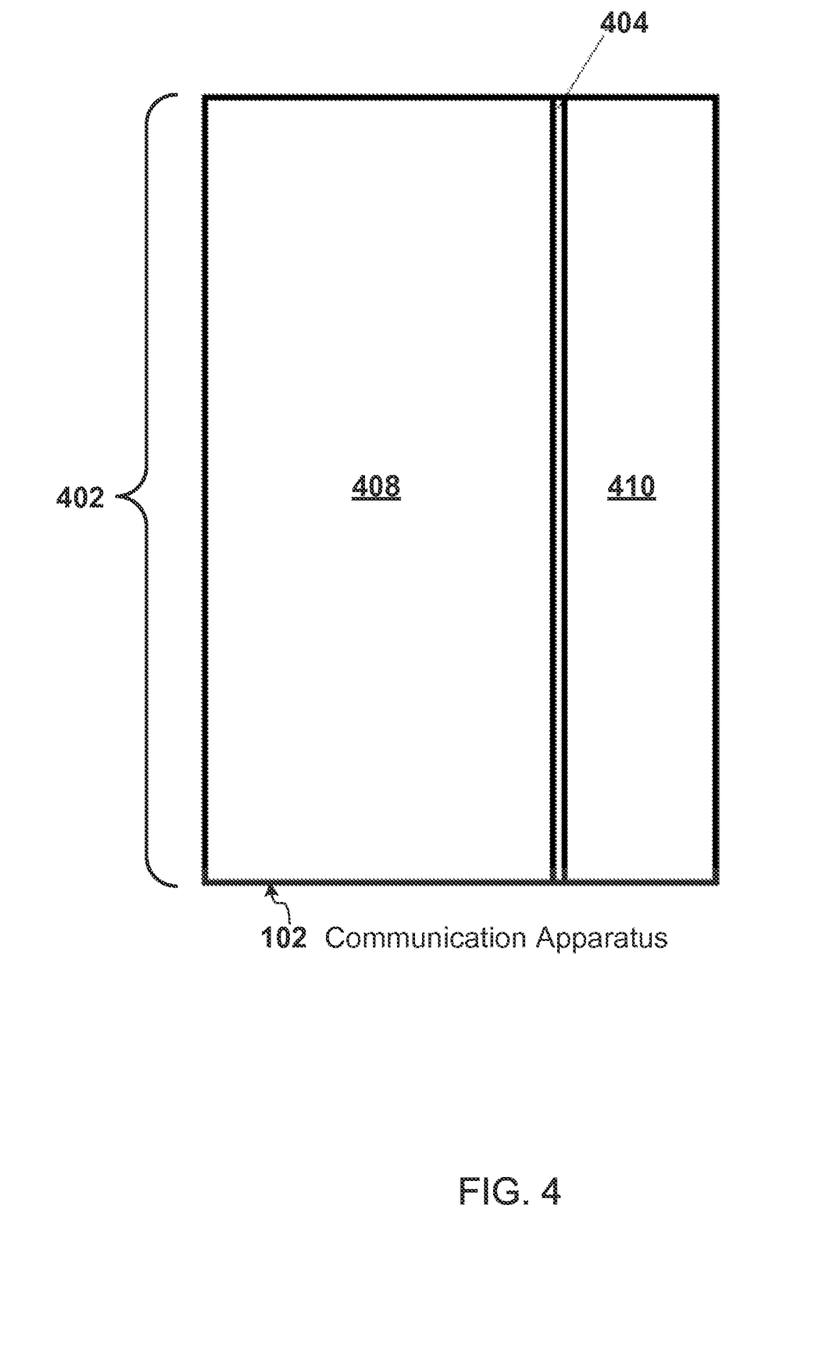
FIG. 4 illustrates a rear view of a communication apparatus that includes a metal cover separated by a thin dielectric forming two cover parts.

FIG. 4 illustrates a rear view of an example of the communication apparatus 102 that includes a conductive cover 402 separated by a thin dielectric 404 forming two cover parts 408 and 410. Each of the cover parts 408 and 410 my serve as a respective one of the antennas 108 and 208. Such an arrangement illustrates how one antenna 108 (one cover part 408) may be proximal to another antenna 208 (the other cover part 410) so that moisture may be detected with the one antenna 108 (for example, cover part 408) broadcasting and the other antenna 208 (for example, cover part 410) receiving. In alternative examples, the cover 402 may form a single antenna from which the impedance sensor 106 may detect the impedance 112 as described above in reference to FIG. 1.

The cover parts 408 and 410 may be part of a housing of the communication apparatus 102. Alternatively or in addition, the cover parts 408 and 410 may be part of a covering of a component that is internal to the communication apparatus 102. Alternatively or in addition, the cover parts 408 and 410 may be part of an attachment that fits over the housing of the communication apparatus 102. The cover parts 408 and 410 may be metal or any conductive material.

When the antennas 108 and 208 are formed from the cover parts 408 and 410, the antennas 108 and 208 may operate as a capacitor in some examples. Indeed, any antenna designs that include at least two antennas having a capacitance may operate as capacitive sensors. An effective series resistance (ESR) may be measured between the two antennas 108 and 208. The EST may represent the impedance 112 at the antenna 208. The lower the ESR, the lower the impedance 112 at the antenna 208. The ESR may correspond to a level of moisture between the antennas 108 and 208.

External antennas may be antennas that are external to the communication apparatus 102, such as the cover parts 408 and 410 illustrated in FIG. 4. External antennas may come in contact with moisture before any other components internal to the communication apparatus 102. Ports (not shown) in the communication apparatus 102 may be the next area to experience an incursion of moisture because ports are the most typical point of water/moisture ingress on an electronic device. A port may be a communication port or any area in which an opening is formed in an outer wall of the communication device 102. Therefore, detecting the impedance 112 at one or more external antennas may help detect moisture before the moisture enters the communication apparatus 102.

The antenna signal 111 may be transmitted periodically and/or without interruption. Cellphones or cellular devices may ping a cell tower periodically. For example, a ping signal may be transmitted from a cellular device at substantially regular intervals. For example, the cellular device may transmit the ping signal every 7 seconds or at another frequency. The ping signal may be received by cellular towers and used to determine a location of the cellular device. The communication apparatus 102 may be in the form of a cellular device in some examples. In order to limit power drain on the battery, the impedance 112 at the antenna 108 or 208 may be measured as the communication apparatus 102 pings the cell tower, essentially piggy-backing the cell tower ping event as a "moisture sense window." In other words, the ping signal carrying data to the cell tower may also serve as the antenna signal 111 from which the impedance sensor 106 detects the impedance 112. The moisture sense window may be the time between two successive transmissions of the antenna signal 111.

An accelerometer or other type of sensor may provide information to the control circuit 110 that may affect the frequency at which the antenna signal 111 is transmitted. The communication apparatus 102 may include an accelerometer (not shown) in some examples. Accelerometer data generated by the accelerometer may be utilized by the control circuit 110 and/or the impedance sensor 106 to trigger the interrogation of the antenna 108 or 208 and/or capacitive-sensor(s) for a predetermined amount of time in response to detection of a free-fall and/or an impact event. During the predetermined amount of time, the moisture sense window may be substantially decreased in order to more quickly detect moisture.

The free-fall event may be an event in which the communication apparatus 102 falls. The impact event may be an event in which the communication apparatus 102 impacts a surface. The free-fall event and/or the impact event may be detected by the accelerometer and/or impact detector.

The predetermined amount of time that the impedance sensor 106 looks for a moisture event after a free-fall even and/or an impact event may be set by an end user via a software app and/or interface. Alternatively or in addition, the amount of time the impedance sensor 106 looks for a moisture event after a free-fall even and/or an impact event may be determined and/or be set to a predetermined value.

In one example of decreasing the moisture sense window, the antenna signal 111 may be initially transmitted at a first frequency. Correspondingly, the impedance 112 at the antenna 108 or 208 may be checked at the first frequency. The first frequency may be the frequency at which a ping signal is transmitted, not the frequency of the ping signal transmitted. Alternatively or in addition, the first frequency may be a frequency between transmissions of the antenna signal 111. In response to detection of the fall event and/or the impact event, the antenna signal 111 may be transmitted by the antenna 108 at a second frequency that is higher than the first frequency. In other words, the impedance at the antenna 108 may be detected at the second frequency, such as constantly or merely at a frequency higher than the first frequency.

A user interface may include one or more user interface element that enables the user to set one or more corresponding accelerometer thresholds. If one or more properties detected by the accelerometer exceed the corresponding accelerometer threshold(s) indicating a fall event and/or an impact event, the control circuit 110 may trigger interrogation of the antenna and/or other sensors in order to detect a potential moisture event.

Figure 5:
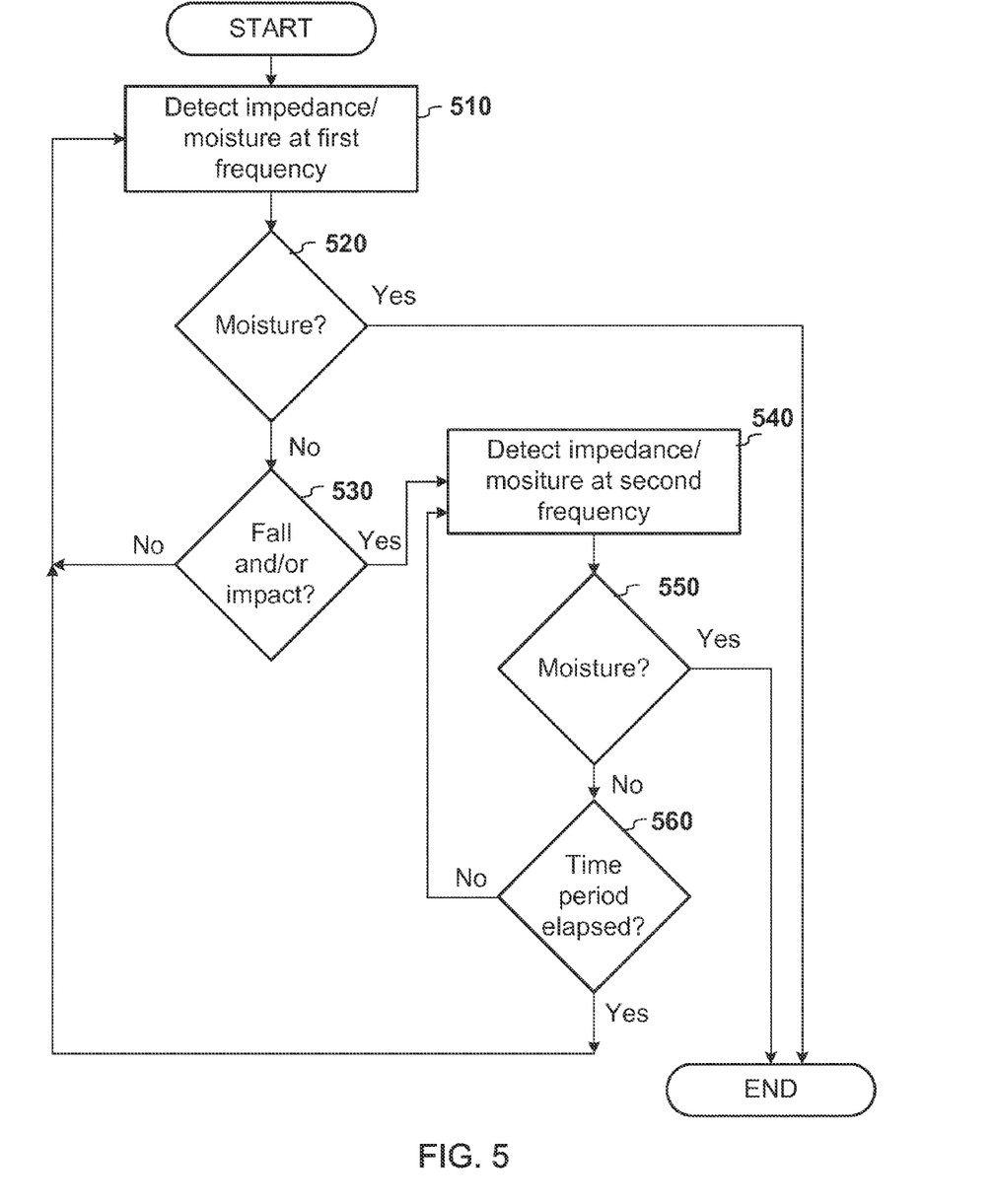
FIG. 5 illustrates a flow diagram of example logic in an antenna-based moisture detection system.

FIG. 5 illustrates a flow diagram of example logic of the system 100 triggered by a free-fall event and/or an impact event. The logic may include additional, different, or fewer operations. The operations may be executed in a different order than illustrated in FIG. 5.

Operations may begin by detecting (510) the impedance 112 at the antenna 108 or 208 (and moisture) at a first frequency. If moisture is detected (520), then operations may end by, for example, transmitting the moisture event 120 indicating moisture is detected.

If no fall event and/or impact event is detected (530) by an accelerometer or other sensor, then operations may continue by detecting (510) the impedance 112 at the antenna 108 or 208 (and moisture) at the first frequency. Alternatively, if a fall event and/or an impact event is detected (530), then operations may continue by detecting (540) the impedance 112 at the antenna 108 or 208 (and moisture) at a second frequency that is higher than the first frequency.

If moisture is detected (550), then operations may end by, for example, transmitting the moisture event 120 indicating moisture is detected. Alternatively, if moisture is not detected (550), then a determination (560) may be made whether a threshold time period has elapsed since the fall event and/or the impact event was detected. If the threshold time period has elapsed, then operations may continue by detecting (510) the impedance 112 at the antenna 108 or 208 at the first frequency instead of the second frequency. However, if the threshold time period has not elapsed, then operations may continue by detecting (540) the impedance 112 at the antenna 108 or 208 (and moisture) at the second frequency.

In some examples, if a detected moisture level exceeds the threshold, then the system 100 may trigger one or more actions. As described in more detail below, the action(s) and/or which of the actions may be customized by the user in some examples.

A user interface may be provided that includes one or more user interface elements through which the user may customize actions that take place in the event that the moisture level exceeds a maximum moisture threshold. One such event may be limiting all or a predetermined set of functions (for example, critical functions) of the communication apparatus 102. Another such event may be shutting down power to all or a subset of the components of the communication apparatus 102. The end user may also designate which functions are disabled or powered off. In some examples, the actions may be broken down to Maximum, Moderate & Minimum moisture protection depending on what functions/components are shut down.

The system 100 may enter a "sleep mode" waiting for the user to take action and/or after sufficient time has elapsed after the moisture event 120 is identified. By entering sleep mode, the power to components of the communication apparatus 102 may be cut off long enough for the moisture to evaporate or otherwise leave the communication apparatus 102. The amount of time that passes after the moisture event 120 is detected and when the device exits the "sleep mode" may also be set by the end user in some examples.

FIG. 6 illustrates an example of the control circuit 110. The control circuit 110 and the impedance sensor 106 are included in a moisture detector 602 in FIG. 6. The moisture detector 602 may be a discrete component separate from the communication apparatus 102. Alternatively, the moisture detector 602 may be included in the communication apparatus 102.

The control circuit 110 may be coupled to the impedance sensor 106 to receive the impedance 112 from the impedance sensor 106. In some examples, the control circuit 110 may be coupled to the signal generator 104.

In addition to being coupled to the control circuit 110, the impedance sensor 106 may be coupled to the antenna 108 in order to detect the impedance 112 at the antenna 108. In some examples, the impedance sensor 106 may be coupled to the signal generator 104 in order to receive the antenna signal 111.

The control circuit 110 may include a processor 604 and memory 606. The memory 606 may include a sensor control module 608, a signal generator control module 610, an impedance-to-moisture converter 612, and a moisture event generator 614.

The processor 604 may be in communication with the memory 606 and the impedance sensor 106. In one example, the processor 604 may also be in communication with additional elements, such as the signal generator 104 and a display (not shown). Examples of the processor 604 may include a general processor, a central processing unit, a microcontroller, an application specific integrated circuit (ASIC), a digital signal processor, a field programmable gate array (FPGA), a digital circuit, and/or an analog circuit.

The processor 604 may be one or more devices operable to execute logic. The logic may include computer executable instructions or computer code embodied in the memory 606 or in other memory that when executed by the processor 604, cause the processor 604 to perform the features implemented by the logic. The computer code may include instructions executable with the processor 604.

The memory 606 may be any device for storing and retrieving computer readable data or any combination thereof. The memory 606 may include non-volatile and/or volatile memory, such as a random access memory (RAM), a read-only memory (ROM), an erasable programmable read-only memory (EPROM), and/or a flash memory. Alternatively or in addition, the memory 606 may include an optical, magnetic (hard-drive) or any other form of data storage device.

The sensor control module 608 in the memory 606 may be component that interacts with one or more sensors, such as with the impedance sensor 106. The sensor control module 608 may receive information from one or more sensors. For example, the sensor control module 608 may receive the impedance 112 from the impedance sensor 106. The sensor control module 608 may receive acceleration data from an accelerometer (not shown).

In some examples, the sensor control module 608 may control one or more parameters of the sensor(s) or otherwise direct the operation of the sensor(s). For example, the sensor control module 608 may control the frequency at which the impedance sensor 106 detects and/or samples the impedance 112.

The signal generator control module 610 may be a component that controls the signal generator 104. For example, the signal generator control module 610 may control the frequency at which the signal generator 104 generates the antenna signal 111. The signal generator control module 610 may specify a wave form or other property that the antenna signal 111 is to have when generated by the signal generator 104.

The impedance-to-moisture converter 612 may be a component that converts the impedance 112, which may have been received by the sensor control module 608, into a corresponding moisture level or other indication of moisture. The impedance-to-moisture converter 612 may perform the conversion with a table, a mathematical equation, and/or any other conversion mechanism.

The moisture event generator 614 may be a component that determines whether to generate the moisture event 120. Alternatively or in addition, the moisture event generator 614 may be a component that generates the moisture event 120.

Figure 7:
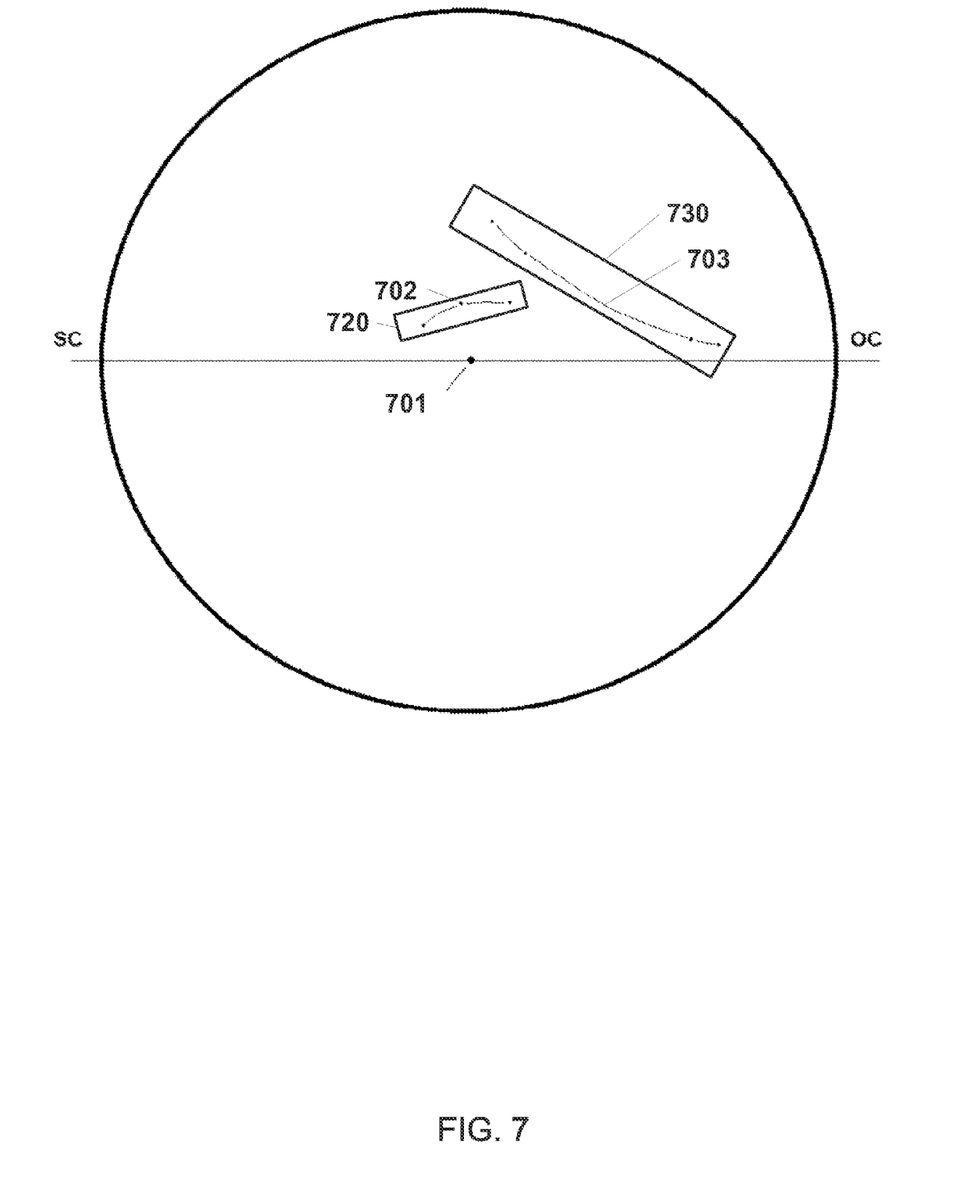
FIG. 7 illustrates a Smith chart of example detected impedances.

FIG. 7 illustrates a Smith chart of example normalized impedances 701, 702, and 703 at the antenna 108 detected by the impedance sensor 106. The normalized impedances 701, 702, and 703 illustrated are for multiple environments in and/or around the communication apparatus 102.

The impedance at the antenna 108 may be referred to as an output impedance and the impedance of an electrical input to the antenna 108, such as the impedance of the signal generator 104, may be referred to as an input impedance. The normalized impedance 701, 702, or 703 may be the detected impedance at the antenna 108 divided by the input impedance or any other characteristic impedance.

As described earlier above, the input impedance may be designed to match the output impedance when the environment is a typical, predetermined environment. As a result, if the environment around the communication apparatus 102 is the predetermined environment that is typical, then the input impedance may be the same as the output impendence (the impedance 112 at the antenna 108) and the normalized impedance 701 may be 1.

On the other hand, if water drops of a predetermined size are placed along the antenna 108, then the normalized impedance 702 may be different than 1. For example, the normalized impedance 702 may be any impedance within a set 720 of impedances that indicates water drops are on the antenna 108.

Similarly, if the antenna 108 and/or the communication apparatus 102 is anywhere from partially immersed to fully immersed in water, then the normalized impedance 703 may be any impedance in a set 730 of impedances that indicates the antenna 108 and/or the communication apparatus 102 is immersed in water.

The control circuit 110 may distinguish between moisture events or between moisture events and non-moisture events by determining which set 720 or 730 of impedances contains the normalized impedance 701, 702, or 703 or actual impedance. For example, if the normalized impedance 701, 702, or 703 is in the set 720 of impedances that indicates drops of water are present on the antenna 108, then the control circuit 110 may generate a moisture event indicating that water drops are detected. As another example, if the normalized impedance 701, 702, or 703 is in the set 730 of impedances that indicates the antenna 108 is immersed in water, then the control circuit 110 may generate a moisture event indicating that the antenna 108 is immersed in water.

The impedance sets 720 and 730 are merely example sets. In other configurations, the control circuit 110 may generate the moisture event based on additional, fewer, or different impedance sets. In addition, the impedance sets 720 and 730 may take any shape on the Smith chart and may be located anywhere in the Smith chart. Although the example illustrated in FIG. 7 is based on normalized impedances, other examples may be based on non-normalized impedances.

The impedance sets 720 and 730 may be determined in a lab. Alternatively, or in addition, the communication apparatus 102 may be configured to configure the impedance sets 720 and 730 based on user input. For example, user input may indicate that water drops are going to be placed on the communication apparatus 102. Water drops may be placed on the apparatus 102, the impedances at the antenna 108 may be detected, and the communication apparatus 102 may generate the impedance set 720 indicating water drops are detected from the detected impedances.

FIG. 1 illustrates one example of the antenna-based moisture detection system 100. The system 100 may include more, fewer, or different elements than illustrated in FIG. 1. For example, the system 100 may include additional sensors, such as an accelerometer, a GPS, and/or a pressure sensor. In another example, instead of including the communication apparatus 102, the system 100 may include the moisture detector 602, which may be installable in, or be installed in, the communication apparatus 102. In yet another example, the system 100 may include only the control circuit 110 or only the control circuit 110 and the impedance sensor 106.

Each component of the system 100 may include additional, different, or fewer components. For example, the signal processor 118 may be included in the control circuit 110 instead of the impedance sensor 106. In another example, none of the components of the system 100 may include the signal processor 118. In yet another example, the impedance sensor 106 and/or the control circuit 110 may include an analog-to-digital converter that converts an analog measurement of the impedance 112 to a digital representation of the impedance 112. In some examples, the control circuit 110 may not include the processor 604. In still other examples, the memory 606 of the control circuit 110 may include an operating system of the communication apparatus, and the signal generator control module 610, the sensor control module 608, the impedance-to-moisture converter 612, and the moisture event generator 614 may be included in an application or app that executes in the operating system. Circuitry may be implemented using dedicated hardware, one or more general purpose processors, digital signal processing circuitry, or any other suitable control circuitry (for example, storage and processing circuitry).

The system 100 may be implemented in many different ways. Each module, such as the impedance sensor 106, the control circuit 110, the signal generator control module 610, the sensor control module 608, the impedance-to-moisture converter 612, and the moisture event generator 614, may be hardware or a combination of hardware and software. For example, each module may include an application specific integrated circuit (ASIC), a Field Programmable Gate Array (FPGA), a circuit, a digital logic circuit, an analog circuit, a combination of discrete circuits, gates, or any other type of hardware or combination thereof. Alternatively or in addition, each module may include memory hardware, such as a portion of the memory 606, for example, that comprises instructions executable with the processor 604 or other processor to implement one or more of the features of the module. When any one of the modules includes the portion of the memory that comprises instructions executable with the processor, the module may or may not include the processor. In some examples, each module may just be the portion of the memory 606 or other physical memory that comprises instructions executable with the processor 604 or other processor to implement the features of the corresponding module without the module including any other hardware. Because each module includes at least some hardware even when the included hardware comprises software, each module may be interchangeably referred to as a hardware module, such as the signal generator control module hardware 610, the sensor control module hardware 608, the impedance-to-moisture converter hardware 612, and the moisture event generator hardware 614.

Some features are shown stored in a computer readable storage medium (for example, as logic implemented as computer executable instructions or as data structures in memory). All or part of the system and its logic and data structures may be stored on, distributed across, or read from one or more types of computer readable storage media. Examples of the computer readable storage medium may include a hard disk, a floppy disk, a CD-ROM, a flash drive, a cache, volatile memory, non-volatile memory, RAM, flash memory, or any other type of computer readable storage medium or storage media. The computer readable storage medium may include any type of non-transitory computer readable storage medium, such as a CD-ROM, a volatile memory, a non-volatile memory, ROM, RAM, or any other suitable storage device.

The processing capability of the system 100 may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL)).

All of the discussion, regardless of the particular implementation described, is exemplary in nature, rather than limiting. For example, although selected aspects, features, or components of the implementations are depicted as being stored in memories, all or part of the system or systems may be stored on, distributed across, or read from other computer readable storage media, for example, secondary storage devices such as hard disks, flash memory drives, floppy disks, and CD-ROMs. Moreover, the various modules and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the logic or instructions are stored in a remote location for transfer through a computer network or over telephone lines. In yet other embodiments, the logic or instructions are stored within a given computer, central processing unit ("CPU"), graphics processing unit ("GPU"), or system.

Furthermore, although specific components are described above, methods, systems, and articles of manufacture described herein may include additional, fewer, or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same program or apparatus. The components may be resident on separate hardware, such as separate removable circuit boards, or share common hardware, such as a same memory and processor for implementing instructions from the memory. Programs may be parts of a single program, separate programs, or distributed across several memories and processors.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations.

What is claimed is:

1. A system for moisture detection, the system comprising:

a communication apparatus;

a housing for the communication apparatus comprising a conductive cover separated by a dielectric, the dielectric separating the conductive cover into a first cover part and a second cover part, wherein the first cover part is a first antenna and the second cover part is a second antenna separated by the dielectric, the first antenna and the second antenna being external to the communication apparatus;

an impedance sensor configured to detect an impedance at the second antenna based on a received signal received through a wave medium from the first antenna, the wave medium being in and around the communication apparatus; and a control circuit configured to detect moisture based on the impedance at the second antenna and transmit a moisture event to a switch that disconnects power to one or more components of the communication apparatus.

2. The system of claim 1, further comprising an accelerometer, wherein the accelerometer is configured to trigger an interrogation of the second antenna in response to detection of a free-fall event, and wherein the received signal is based on an antenna signal transmitted from the first antenna.

3. The system of claim 2, wherein the impedance is determined by the impedance sensor as an effective series resistance between the first antenna and the second antenna.

4. The system of claim 2, wherein the first antenna is a cellular network antenna and the antenna signal is a ping signal transmitted at substantially regular intervals.

5. The system of claim 2, wherein the impedance sensor is configured to determine the impedance based on a comparison of the antenna signal and the received signal.

6. The system of claim 1, wherein the impedance sensor is configured to derive the impedance from a voltage and/or a current of a signal received by the second antenna.

7. A non-transitory computer readable storage medium comprising computer executable instructions, the computer executable instructions executable by a processor, the computer executable instructions comprising:

instructions executable to transmit an antenna signal from a first cover part of a housing for a communication apparatus, wherein the first cover part is a first antenna, to a second cover part of the housing, wherein the second cover part is a second antenna, the first antenna and the second antenna forming part of the housing for the communication apparatus and being separated by a dielectric, the first antenna and the second antenna being external to the communication apparatus;

instructions executable to receive an impedance from an impedance sensor, wherein the impedance is electrical impedance at the second antenna detected by the impedance sensor and based on a received signal received through a wave medium from the first antenna, the wave medium being in and around the communication apparatus; and instructions executable to detect moisture based on the impedance at the second antenna and transmit a moisture event to a switch that disconnects power to one or more components of the communication apparatus.

8. The computer readable storage medium of claim 7, wherein the moisture is detected in response to a magnitude of the impedance at the second antenna falling below a threshold magnitude.

9. The computer readable storage medium of claim 7, wherein the moisture is detected in response to a decrease in the impedance detected by the impedance sensor over time.

10. The computer readable storage medium of claim 7, wherein the moisture is detected as a moisture level, which is determined from a mapping of the impedance to the moisture level.

11. The computer readable storage medium of claim 7, wherein the moisture is detected in response to detection of a pattern of impedance changes across multiple frequencies.

12. The computer readable storage medium of claim 7 further comprising instructions executable to determine the impedance in response to detection, by the impedance sensor, of signals reflected by the second antenna due to an impedance mismatch between the second antenna and a signal generator.

13. The computer readable storage medium of claim 7, wherein the impedance is an indication of impedance and/or an indication of a change in the impedance.

14. A method to detect moisture with an antenna, the method comprising:

transmitting an antenna signal from a first cover part of a housing for a communication apparatus, wherein the first cover part is a first antenna, to a second cover part of the housing, wherein the second cover part is a second antenna, the first antenna and the second antenna forming part of the housing for the communication apparatus and being separated by a dielectric, the first antenna and the second antenna being external to the communication apparatus;

detecting, by an impedance sensor, an impedance at the second antenna based on a received signal received through a wave medium from the first antenna, the wave medium being in and around the communication apparatus; and detecting moisture with a processor based on the impedance at the second antenna wherein the moisture is detected in response to a decrease in the impedance detected by the impedance sensor over time; and transmitting a moisture event to a switch that disconnects power to one or more components of the communication apparatus.

15. The method of claim 14, wherein the antenna signal has a voltage and a current, and wherein detecting the impedance comprises determining the impedance by dividing the voltage by the current.

16. The method of claim 15, wherein in the antenna signal is transmitted at a first frequency, the method further comprising transmitting the antenna signal at a second frequency in response to detection of a fall and/or an impact of the communication apparatus, the communication apparatus including the first antenna, the second antenna, the impedance sensor, and the processor, and wherein the communication apparatus is a mobile phone.

* * * * *